(12) United States Patent
Phillips

(10) Patent No.: US 9,468,428 B2
(45) Date of Patent: Oct. 18, 2016

(54) HEMOSTATIC DEVICE AND ITS METHODS OF USE

(75) Inventor: Victor Matthew Phillips, Jefferson City, MO (US)

(73) Assignee: Phillips Medical LLC, Jefferson City, MO (US)

( * ) Notice: Subject to any disclaimer, the term of this patent is extended or adjusted under 35 U.S.C. 154(b) by 0 days.

(21) Appl. No.: 13/495,714

(22) Filed: Jun. 13, 2012

(65) Prior Publication Data

US 2013/0338705 A1 Dec. 19, 2013

(51) Int. Cl.
*A61B 17/03* (2006.01)
*A61B 17/00* (2006.01)

(52) U.S. Cl.
CPC .... *A61B 17/0057* (2013.01); *A61B 2017/0065* (2013.01); *A61B 2017/00637* (2013.01); *A61B 2017/00672* (2013.01)

(58) Field of Classification Search
CPC .............. A61B 17/03; A61B 17/0057; A61B 17/00491; A61B 2017/00601; A61B 2017/0065; A61B 2017/00654; A61B 2017/00672; A61B 2017/00637; A61M 25/1002; A61M 2202/045; A61M 2025/1052
USPC .................... 604/264, 265, 11; 606/213, 229
See application file for complete search history.

(56) References Cited

U.S. PATENT DOCUMENTS

| | | | |
|---|---|---|---|
| 4,738,658 A | 4/1988 | Magro et al. | |
| 4,850,960 A | 7/1989 | Grayzel | |
| 4,890,612 A | 1/1990 | Kensey | |
| 4,895,564 A | 1/1990 | Farrell | |
| 4,929,246 A | 5/1990 | Sinofsky | |
| 5,061,274 A | 10/1991 | Kensey | |
| 5,108,421 A | 4/1992 | Fowler | |
| 5,201,756 A * | 4/1993 | Horzewski et al. | 606/198 |
| 5,222,974 A | 6/1993 | Kensey et al. | |
| 5,282,827 A | 2/1994 | Kensey et al. | |
| 5,290,310 A | 3/1994 | Makower et al. | |
| 5,306,254 A | 4/1994 | Nash et al. | |
| 5,326,350 A | 7/1994 | Li | |
| RE34,866 E | 2/1995 | Kensey et al. | |
| 5,391,183 A | 2/1995 | Janzen et al. | |
| 5,415,657 A | 5/1995 | Taymor-Luria | |
| 5,431,639 A * | 7/1995 | Shaw | 604/264 |
| 5,437,292 A | 8/1995 | Kipshidze et al. | |
| 5,437,631 A | 8/1995 | Janzen | |
| 5,441,517 A | 8/1995 | Kensey et al. | |
| 5,443,481 A | 8/1995 | Lee | |
| 5,486,195 A * | 1/1996 | Myers et al. | 606/213 |
| 5,591,204 A | 1/1997 | Janzen et al. | |

(Continued)

FOREIGN PATENT DOCUMENTS

WO 2011133395 A1 10/2011

OTHER PUBLICATIONS

International Search Report and Written Opinion of International Application No. PCT/US2013/043681; Sep. 5, 2013; 13 ages.

(Continued)

*Primary Examiner* — Katherine Rodjom
(74) *Attorney, Agent, or Firm* — Armstrong Teasdale LLP

(57) ABSTRACT

A hemostatic device includes an injection tube having at least one distal tube opening configured to discharge a first fluid to facilitate sealing the puncture. A guide is adjacent a distal end of the injection tube. The guide includes a cone-shaped portion having an apex oriented towards a distal end of the hemostatic device.

20 Claims, 4 Drawing Sheets

(56) References Cited

U.S. PATENT DOCUMENTS

| | | |
|---|---|---|
| 5,645,566 A | 7/1997 | Brenneman et al. |
| 5,653,730 A | 8/1997 | Hammerslag |
| 5,665,107 A | 9/1997 | Hammerslag |
| 5,676,689 A * | 10/1997 | Kensey ............ A61B 17/0057 604/168.01 |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,766,157 A | 6/1998 | Tilton, Jr. |
| 5,766,206 A | 6/1998 | Wijkamp et al. |
| 5,782,861 A | 7/1998 | Cragg et al. |
| 5,843,124 A | 12/1998 | Hammerslag |
| 5,868,762 A | 2/1999 | Cragg et al. |
| 5,935,147 A | 8/1999 | Kensey et al. |
| 5,951,583 A | 9/1999 | Jensen et al. |
| 5,984,950 A | 11/1999 | Cragg et al. |
| 6,045,570 A | 4/2000 | Epstein et al. |
| 6,056,768 A | 5/2000 | Cates et al. |
| 6,090,130 A | 7/2000 | Nash et al. |
| 6,296,657 B1 | 10/2001 | Brucker |
| 6,302,898 B1 * | 10/2001 | Edwards et al. ............ 606/214 |
| 6,315,753 B1 | 11/2001 | Cragg et al. |
| 6,325,789 B1 | 12/2001 | Janzen et al. |
| 6,371,974 B1 | 4/2002 | Brenneman et al. |
| 6,371,975 B2 | 4/2002 | Cruise et al. |
| 6,527,734 B2 | 3/2003 | Cragg et al. |
| 6,544,236 B1 | 4/2003 | Cragg et al. |
| 6,547,806 B1 * | 4/2003 | Ding ............ 606/213 |
| 6,610,026 B2 | 8/2003 | Cragg et al. |
| 6,743,248 B2 * | 6/2004 | Edwards et al. ............ 606/214 |
| 6,830,756 B2 | 12/2004 | Hnojewyj |
| 6,863,680 B2 | 3/2005 | Ashby |
| 6,984,219 B2 * | 1/2006 | Ashby et al. ............ 604/15 |
| 7,029,489 B1 | 4/2006 | Ashby et al. |
| 7,037,322 B1 | 5/2006 | Sing et al. |
| 7,048,710 B1 | 5/2006 | Cragg et al. |
| 7,201,725 B1 | 4/2007 | Cragg et al. |
| 7,318,933 B2 | 1/2008 | Hnojewyj |
| 7,335,219 B1 | 2/2008 | Ashby et al. |
| 7,455,680 B1 | 11/2008 | Ashby et al. |
| 7,611,479 B2 | 11/2009 | Cragg et al. |
| 7,625,352 B1 | 12/2009 | Ashby et al. |
| 2001/0018598 A1 | 8/2001 | Cruise et al. |
| 2002/0077658 A1 * | 6/2002 | Ginn ............ 606/213 |
| 2003/0088271 A1 | 5/2003 | Cragg et al. |
| 2003/0100921 A1 | 5/2003 | Addis et al. |
| 2004/0019328 A1 | 1/2004 | Sing et al. |
| 2004/0098024 A1 | 5/2004 | Dieck et al. |
| 2004/0102730 A1 | 5/2004 | Davis et al. |
| 2004/0176801 A1 | 9/2004 | Edwards et al. |
| 2006/0100664 A1 | 5/2006 | Pai et al. |
| 2006/0116635 A1 * | 6/2006 | Van Heugten ..... A61B 17/0057 604/103.01 |
| 2006/0276838 A1 | 12/2006 | Wensel et al. |
| 2007/0038245 A1 | 2/2007 | Morris et al. |
| 2007/0123816 A1 | 5/2007 | Zhu et al. |
| 2008/0038313 A1 | 2/2008 | Addis et al. |
| 2008/0046005 A1 | 2/2008 | Lenker et al. |
| 2008/0071310 A1 | 3/2008 | Hoffman et al. |
| 2008/0082122 A1 | 4/2008 | Khosravi et al. |
| 2008/0161849 A1 | 7/2008 | Cates et al. |
| 2009/0088793 A1 | 4/2009 | Bagaoisan et al. |
| 2009/0143808 A1 | 6/2009 | Houser |
| 2009/0171282 A1 | 7/2009 | Pipenhagen et al. |
| 2011/0137338 A1 * | 6/2011 | Phillips ............ 606/213 |

OTHER PUBLICATIONS

Extended European Search Report, dated Mar. 2, 2016, for co-pending European patent application No. EP 13805060.4 (7 pgs.).

* cited by examiner

HEMOSTATIC DEVICE AND ITS METHODS OF USE

BACKGROUND OF THE INVENTION

The subject matter described herein relates generally to medical devices and, more particularly, to a hemostatic device.

Catheter introducers are known to provide an access site to an artery for at least some medical procedures such as cardiac catheterizations or peripheral endovascular procedures. After such medical procedures are conducted, the catheter introducer is removed from the access site, leaving an arterial opening. Generally, excess blood loss endangers and/or traumatizes the patient. One known method of controlling blood loss is through direct manual pressure over the access site.

BRIEF SUMMARY OF THE INVENTION

In one aspect, a method is provided for using a hemostatic device to seal a puncture of a vessel. The hemostatic device includes an injection tube and a guide adjacent a distal end of the injection tube. The method includes advancing the hemostatic device through the puncture until the guide is positioned outside and substantially adjacent the vessel. The guide includes a cone-shaped portion having an apex oriented towards a distal end of the hemostatic device. The method further includes discharging a first fluid from at least one distal tube opening of the injection tube to facilitate sealing the puncture, and withdrawing the hemostatic device from the puncture.

In another aspect, a hemostatic device is provided for sealing a puncture of a vessel. The hemostatic device includes an injection tube having at least one distal tube opening configured to discharge a first fluid to facilitate sealing the puncture. A guide is adjacent a distal end of the injection tube. The guide includes a cone-shaped portion having an apex oriented towards a distal end of the hemostatic device.

In yet another aspect, a system is provided for sealing a puncture of a vessel. The system includes a guidewire and a hemostatic device including an injection tube and a guide adjacent a distal end of the injection tube. The injection tube has at least one distal tube opening configured to discharge a first fluid to facilitate sealing the puncture. The guide includes a cone-shaped portion having an apex oriented towards a distal end of the hemostatic device. The hemostatic device is configured to be advanced along the guidewire.

The features, functions, and advantages described herein may be achieved independently in various embodiments of the present disclosure or may be combined in yet other embodiments, further details of which may be seen with reference to the following description and drawings.

Although specific features of various embodiments may be shown in some drawings and not in others, this is for convenience only. Any feature of any drawing may be referenced and/or claimed in combination with any feature of any other drawing.

DETAILED DESCRIPTION OF THE INVENTION

The methods and apparatus described herein relate to medical devices and, more particularly, to a hemostatic device. The hemostatic device described herein enables a puncture of a vessel to be sealed. More particularly, the hemostatic device described herein enables an injection tube to be precisely positioned outside and substantially adjacent the vessel. A hemocoagulant agent is injected through the injection tube to facilitate sealing the puncture, thereby reducing a time required for hemostasis and ambulation.

As used herein, an element or step recited in the singular and proceeded with the word "a" or "an" should be understood as not excluding plural elements or steps unless such exclusion is explicitly recited. Furthermore, references to "one embodiment" of the present invention or the "exemplary embodiment" are not intended to be interpreted as excluding the existence of additional embodiments that also incorporate the recited features.

Figure 1:
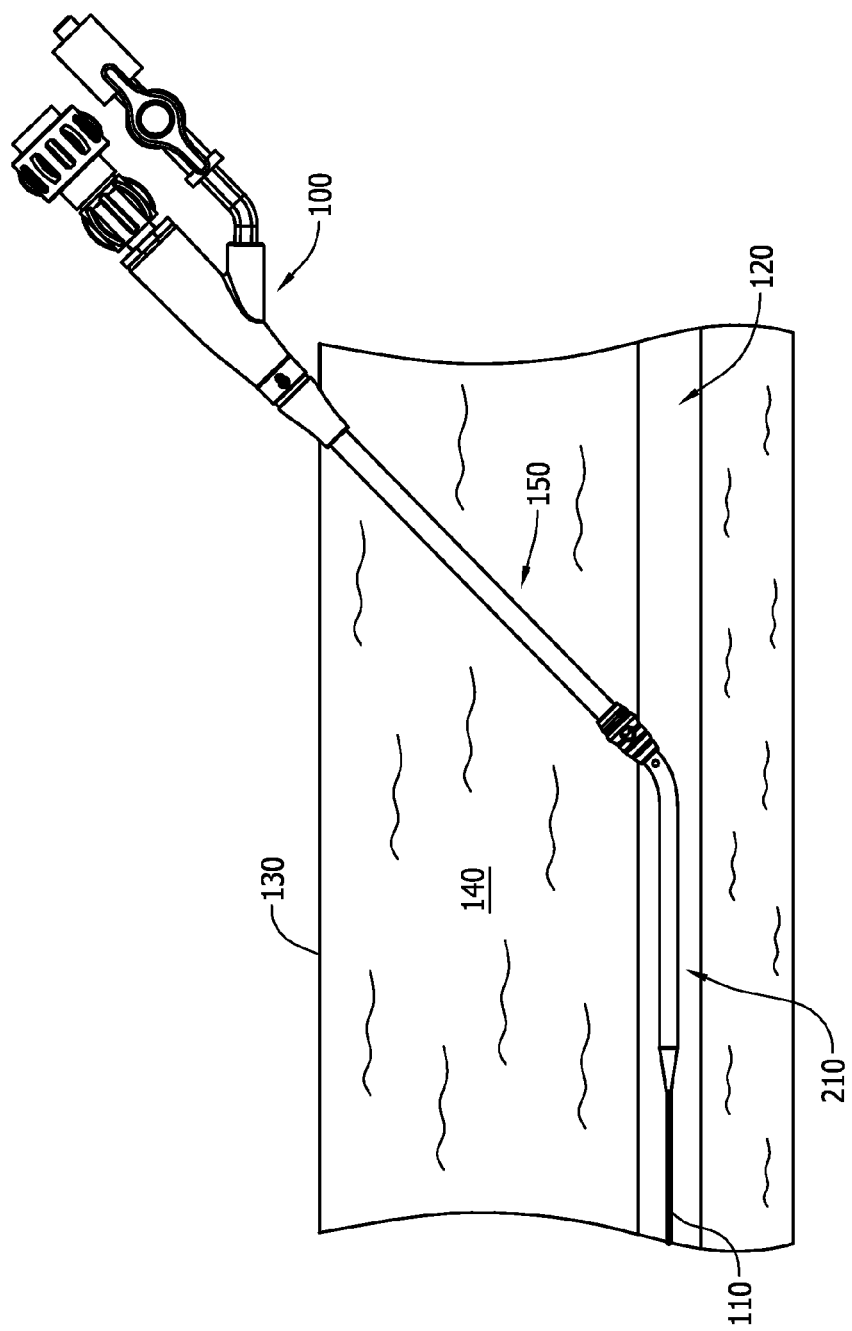
FIG. 1 is a partial cross-sectional view of an access site including an exemplary hemostatic device.
Figure 2:
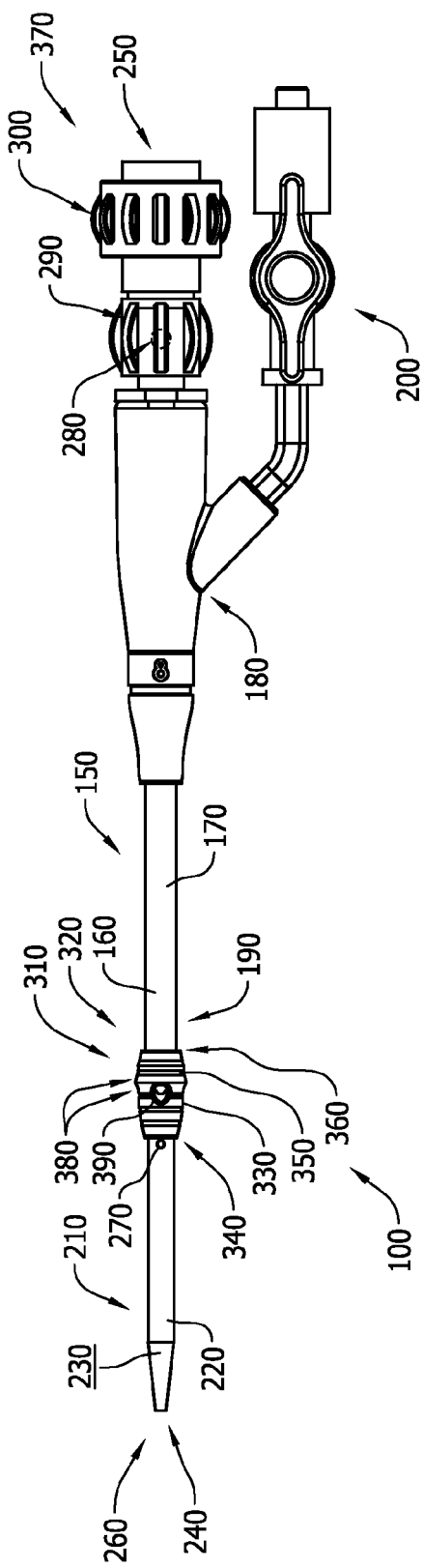
FIG. 2 is a perspective view of the hemostatic device shown in FIG. 1.

FIG. 1 is a partial cross-sectional view of an access site including an exemplary hemostatic device 100, a guidewire 110, and a vessel 120 under a skin surface 130 within subcutaneous tissue 140. For example, vessel 120 may be, without limitation, an artery. FIG. 2 is a perspective view of hemostatic device 100. In the exemplary embodiment, hemostatic device 100 is configured to be advanced along guidewire 110 to facilitate sealing a puncture of vessel 120. In the exemplary embodiment, hemostatic device 100 has a length of at least approximately 10.0 centimeters (cm) (3.94 inches (in.)). More particularly, the length is approximately 20 cm (7.87 in.). Alternatively, hemostatic device 100 may have any length that enables hemostatic device 100 to function as described herein.

In the exemplary embodiment, hemostatic device 100 includes an injection tube 150. In the exemplary embodiment, injection tube 150 includes a tube sidewall 160 that at least partially defines an outer tube lumen 170 therein. In the exemplary embodiment, a proximal tube opening 180 and at least one distal tube opening 190 are in fluid communication with tube lumen 170 to enable a first fluid to be channeled through outer tube lumen 170. More particularly, a plurality of distal tube openings 190 are spaced substantially evenly about a circumference of injection tube 150. For example, the first fluid may include, without limitation, a hemocoagulant agent, a sealant, and/or a flowable gelatin that is configured to seal the access site. In the exemplary embodiment, proximal tube opening 180 and/or distal tube opening 190 extend radially through tube sidewall 160. Alternatively, injection tube 150 may have any number of proximal tube openings 180 and/or distal tube openings 190 in any arrangement and/or orientation that enables injection tube 150 to function as described herein.

In the exemplary embodiment, hemostatic device 100 includes a tube valve 200 that is actuatable between a closed configuration and an open configuration. For example, tube valve 200 may be a stop cock. More particularly, tube valve 200 is actuatable towards the open configuration to selectively provide access to proximal tube opening 180. In the exemplary embodiment, tube valve 200 enables proximal tube opening 180 to be at least partially opened such that a flow of the first fluid through tube lumen 170 and/or distal tube opening 190 is increased. For example, a syringe (not shown) may inject the first fluid into proximal tube opening 180 through tube valve 200. In the exemplary embodiment, tube valve 200 is actuatable towards the closed configuration to selectively restrict access to proximal tube opening 180. Tube valve 200 enables proximal tube opening 180 to be at least partially closed such that a flow of the first fluid through tube lumen 170 and/or distal tube opening 190 is decreased.

In the exemplary embodiment, hemostatic device 100 includes a locator device 210 that includes a device sidewall 220 defining a device lumen 230 therein. In the exemplary embodiment, device sidewall 220 is sized to receive guidewire 110 within device lumen 230. More particularly, a distal end opening 240 and/or a proximal end opening 250 are in fluid communication with device lumen 230 and are sized such that guidewire 110 is longitudinally extendable through device lumen 230 between distal end opening 240 and proximal end opening 250. In the exemplary embodiment, distal end opening 240 and/or proximal end opening 250 are defined by device sidewall 220 and have a diameter that is greater than and/or substantially equal to a diameter of guidewire 110. For example, the diameter may be approximately 0.089 cm (0.035 in.). Alternatively, distal end opening 240 and/or proximal end opening 250 may have any diameter that enables guidewire 110 and/or locator device 210 to function as described herein.

In the exemplary embodiment, a distal end 260 of hemostatic device 100 is tapered to facilitate traversing locator device 210 through subcutaneous tissue 140 and into vessel 120. In one embodiment, an outer diameter of locator device 210 is approximately 0.251 cm (0.099 in.) for a 6 French (Fr) system. In another embodiment, the outer diameter is approximately 0.318 mm (0.125 in.) for an 8 Fr system. Alternatively, locator device 210 may have any outer diameter that enables locator device to function as described herein.

In the exemplary embodiment, locator device 210 extends substantially coaxially and/or concentrically with injection tube 150 such that tube lumen 170 is defined between an inner surface of tube sidewall 160 and an outer surface of device sidewall 220. That is, in the exemplary embodiment, injection tube 150 is an outer tube, and locator device 210 is an inner tube. Alternatively, injection tube 150 and/or locator device 210 may extend in any orientation that enables hemostatic device 100 to function as described herein.

In the exemplary embodiment, a distal device opening 270 and a proximal end opening 250 are in fluid communication with device lumen 230 to enable a second fluid to be channeled through device lumen 230. For example, the second fluid may include, without limitation, blood from vessel 120. Additionally or alternatively, distal device opening 270 and a proximal device opening 280 (shown in shadow lines) are in fluid communication with device lumen 230 to enable the second fluid to be channeled through device lumen 230. In the exemplary embodiment, distal device opening 270 and/or proximal device opening 280 extend radially through device sidewall 220.

In the exemplary embodiment, device lumen 230 has a first portion between distal end opening 240 and distal device opening 270, and a second portion between distal device opening 270 and proximal end opening 250. In the exemplary embodiment, distal device opening 270 is positioned approximately 3.15 in. (8.0 cm) from distal end 260. In the exemplary embodiment, the first portion has a diameter that is substantially similar to the diameter of distal end opening 240, and the second portion has a diameter that is greater than the diameter of the first portion. For example, the first portion may have a diameter that is approximately 0.089 cm (0.035 in.), and the second portion may have a diameter that is approximately 0.132 cm (0.052 in.). Alternatively, locator device 210 may have any number of distal device openings 270 and/or proximal device openings 280 having any size and/or shape and in any position, arrangement, and/or orientation that enables locator device 210 to function as described herein.

In the exemplary embodiment, hemostatic device 100 includes a first device valve 290 actuatable between an open configuration and a closed configuration. More particularly, first device valve 290 is actuatable towards the closed configuration to selectively restrict access to proximal device opening 280. That is, in the exemplary embodiment, first device valve 290 enables proximal device opening 280 to be at least partially closed such that a flow of the second fluid through device lumen 230 and/or distal device opening 270 is decreased. Moreover, in the exemplary embodiment, first device valve 290 is actuatable towards the open configuration to selectively provide access to proximal device opening 280. That is, in the exemplary embodiment, first device valve 290 enables proximal device opening 280 to be at least partially opened such that a flow of the second fluid through device lumen 230 and/or distal device opening 270 is increased.

In the exemplary embodiment, hemostatic device 100 includes a second device valve 300 actuatable between an open configuration and a closed configuration. More particularly, second device valve 300 is actuatable towards the closed configuration to selectively restrict access to proximal end opening 250. In the exemplary embodiment, second device valve 300 enables proximal end opening 250 to be at least partially closed such that a flow of the second fluid through device lumen 230 and/or distal device opening 270 is decreased. In the exemplary embodiment, second device valve 300 is actuatable towards the open configuration to selectively provide access to proximal end opening 250. Second device valve 300 enables proximal end opening 250 to be at least partially opened such that a flow of the second fluid through device lumen 230 and/or distal device opening 270 is increased. Moreover, second device valve 300 enables a guidewire to be positioned within proximal end opening 250, device lumen 230, and/or device end opening 240.

Figure 3:
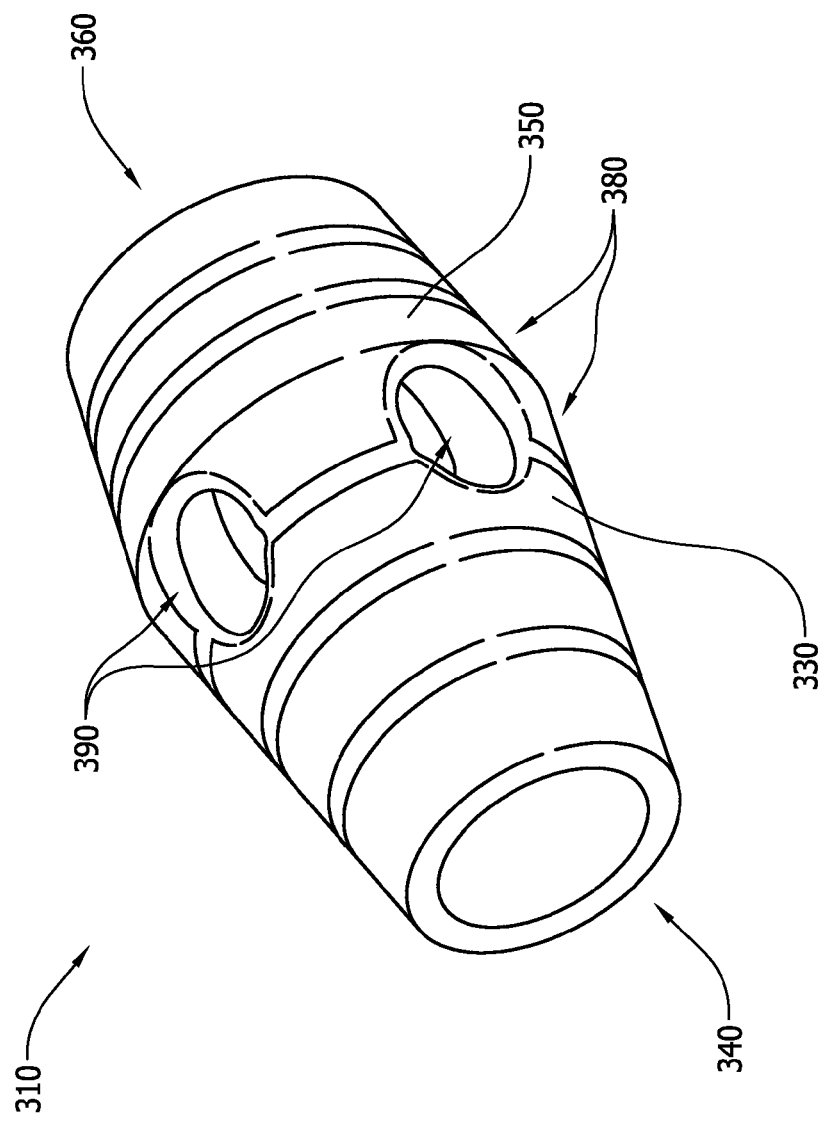
FIG. 3 is a perspective view of an exemplary guide that may be used with the hemostatic device shown in FIG. 1.

In the exemplary embodiment, hemostatic device 100 includes a guide 310 adjacent a distal end 320 of injection tube 150. FIG. 3 is a detailed perspective view of guide 310. In the exemplary embodiment, guide 310 is fabricated from a soft and/or pliable material that enables a seal to be provided at the access site. For example, guide 310 may be fabricated from, without limitation, rubber and/or a rubber-like material. In the exemplary embodiment, guide 310 includes a distal portion 330 having a distal apex 340 oriented towards distal end 260 of hemostatic device 100, and a proximal portion 350 having a proximal apex 360 oriented towards a proximal end 370 of hemostatic device 100 such that the bases 380 of portions 330 and 350 are facing each other. In the exemplary embodiment, distal portion 330 and/or proximal portion 350 are cone-shaped to facilitate traversing guide 310 through subcutaneous tissue 140.

In the exemplary embodiment, guide 310 is coupled to injection tube 150 and/or locator device 210 such that distal tube opening 190 and/or guide 310 are positionable outside and substantially adjacent vessel 120 when distal device opening 270 is within vessel 120. Guide 310 extends between distal tube opening 190 and distal device opening 270 and has a length of approximately 1.0 cm (0.39 in.). In an alternative embodiment, guide 310 may have any length that enables hemostatic device 100 to function as described herein.

In the exemplary embodiment, distal portion 330 generally circumscribes locator device 210, and proximal portion 350 generally circumscribes injection tube 150. More particularly, distal portion 330 and/or proximal portion 350 are aligned substantially coaxially and/or concentrically with injection tube 150 and/or locator device 210. In the exemplary embodiment, distal portion 330 includes at least one guide opening 390 that is positioned and/or aligned to be in fluid communication with distal tube opening 190. More particularly, guide openings 390 are spaced substantially evenly about a circumference of guide 310. In the exemplary embodiment, guide openings 390 are angled towards vessel 120. For example, guide openings 390 may be angled at an approximately 45 degree angle with respect to a longitudinal axis of guide 310. Alternatively, guide 310 may have any number of guide openings 390 in any arrangement and/or orientation that enables guide 310 to function as described herein.

Figure 4:
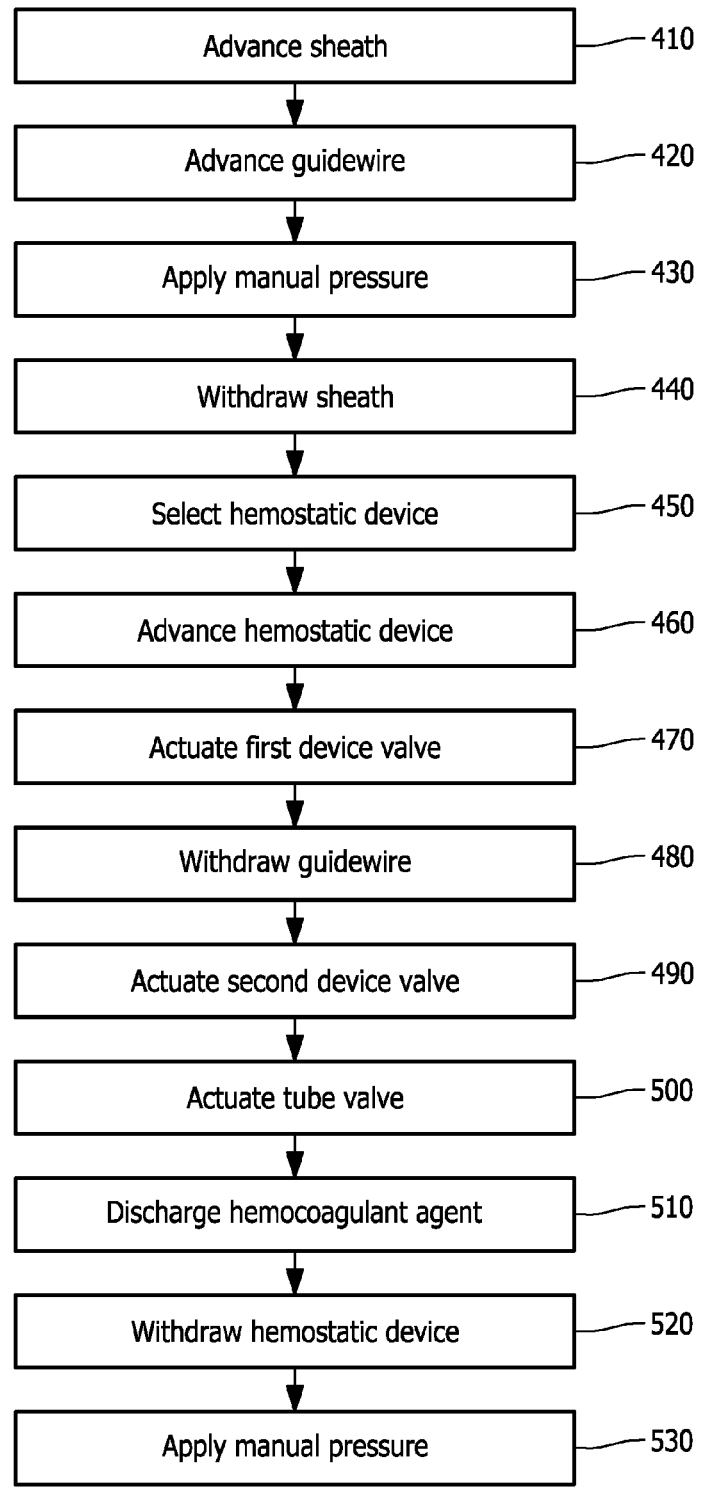
FIG. 4 is a flow chart illustrating an exemplary method using the hemostatic device shown in FIG. 1.

FIG. 4 is a flow chart illustrating an exemplary method 400 using hemostatic device 100 to seal a puncture of vessel 120. In the exemplary embodiment, a sheath (not shown) used during a medical procedure, such as a cardiac catheterization or a peripheral endovascular procedure, is advanced 410 such that a tip of the sheath is approximately 10.0 cm (3.94 in.) from the access site and the sheath is free of at least some devices. In the exemplary embodiment, guidewire 110 is advanced 420 through the sheath to vessel 120 such that a tip of guidewire 110 is positioned at least approximately 5.0 cm (1.97 in.) beyond the tip of the sheath. More particularly, the tip of guidewire 110 is positioned approximately 10.0 cm (3.94 in.) beyond the tip of the sheath. Alternatively, the tip of guidewire 110 may be advanced any distance beyond the tip of sheath that enables hemostatic device 100 to function as described herein. In the exemplary embodiment, manual pressure is applied 430 over the access site, and the sheath is withdrawn 440 from the access site over guidewire 110.

In the exemplary embodiment, hemostatic device 100 is selected 450 based on an outer diameter of hemostatic device 100 and/or the sheath. For example, a 6 Fr hemostatic device 100 may be selected 450 for use with a sheath having a diameter between approximately 4 Fr and 6 Fr, and an 8 Fr hemostatic device 100 may be selected 450 for use with a sheath having a diameter between approximately 6 Fr and 8 Fr. In the exemplary embodiment, hemostatic device 100 may be used with sheaths having diameters that are between approximately 4 Fr and approximately 9 Fr. Alternatively, hemostatic device 100 may be used with a sheath having any diameter that enables hemostatic device 100 to function as described herein.

In the exemplary embodiment, hemostatic device 100 is advanced 460 through subcutaneous tissue 140 until guide 310 and/or injection tube distal end 320 is positioned outside and substantially adjacent vessel 120 and/or blood discharges from proximal end opening 250 and/or proximal device opening 280. More particularly, hemostatic device 100 is advanced 460 along guidewire 110 through subcutaneous tissue 140 and into vessel 120 until distal device opening 270 is positioned within vessel 120, wherein blood flows into distal device opening 270, is channeled through device lumen 230, and/or is discharged from proximal end opening 250 and/or proximal device opening 280. In the exemplary embodiment, guide 310 provides tactile feedback and the blood provides visual feedback to facilitate advancing 460 hemostatic device 100 a desired distance and/or ensuring that distal tube opening 190 remains extraluminal.

To reduce an amount of blood that is discharged from proximal device opening 280, first device valve 290 is actuated 470 towards the closed configuration to selectively restrict access to proximal device opening 280. Moreover, in the exemplary embodiment, guidewire 110 is withdrawn 480 from vessel 120 and/or hemostatic device 100, and second device valve 300 is actuated 490 towards the closed configuration to selectively restrict access to proximal end opening 250.

With injection tube distal end 320 positioned outside and substantially adjacent vessel 120, tube valve 200 is actuated 500 towards the open configuration, and a hemocoagulant agent is discharged 510 from distal tube opening 190 along a tract through subcutaneous tissue 140 to facilitate sealing the puncture. More particularly, a syringe (not shown) injects the hemocoagulant agent into proximal tube opening 180 through tube valve 200, and the hemocoagulant agent is channeled through tube lumen 170 and discharged 510 from distal tube opening 190. In at least some embodiments, contrast may be injected into proximal tube opening 180 through tube valve 200 under fluoroscopy prior to the injection of the hemocagulant agent to enable a desired position of distal tube opening 190 to be verified. In the exemplary embodiment, distal apex 340 provides a seal that facilitates restricting the hemocoagulant agent from flowing into vessel 120.

In the exemplary embodiment, the hemocoagulant agent may be systematically discharged 510 as hemostatic device 100 is withdrawn 520 from subcutaneous tissue 140. More particularly, hemostatic device 100 is systematically positioned at a plurality of predetermined locations, wherein the hemocoagulant agent is discharged 510 from distal tube opening 190. In one embodiment, an indicator (not shown) provides visual feedback to facilitate systematically positioning hemostatic device 100 at each of the plurality of predetermined locations. For example, the indicator may be a plurality of marks on an outer surface of hemostatic device 100 that are spaced approximately 1.0 cm (0.394 in.) apart. Additionally or alternatively, hemostatic device 100 may be rotated about a longitudinal axis at each of the plurality of predetermined locations. In the exemplary embodiment, direct, non-occlusive manual pressure is continuously applied 530 to the access site when hemostatic device 100 is withdrawn 520 from the access site until hemostasis is achieved.

The subject matter described herein relates to medical devices and, more particularly, to a hemostatic device. The hemostatic device described herein enables a puncture of a vessel to be sealed to facilitate controlling blood loss. More particularly, the hemostatic device described herein enables an injection tube to be positioned outside and substantially adjacent the vessel. A sealant and/or flowable gelatin is injected through the injection tube to facilitate sealing the puncture, thereby reducing a time required for manual compression and/or hemostasis. Accordingly, the hemostatic device described herein enables faster patient ambulation and earlier patient discharge.

Exemplary embodiments of a hemostatic device and its methods of use are described above in detail. The systems and methods are not limited to the specific embodiments described herein, but rather, components of systems and/or steps of the methods may be utilized independently and separately from other components and/or steps described herein. Each component and each method step may also be used in combination with other components and/or method steps. Although specific features of various embodiments may be shown in some drawings and not in others, this is for convenience only. Any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for using a hemostatic device for sealing a puncture of a vessel, the hemostatic device including an injection tube and a guide adjacent a distal end of the injection tube, the guide including a cone-shaped portion having an apex oriented towards a distal end of the hemostatic device and at least one guide opening defined in the cone-shaped portion in fluid communication with at least one distal opening of the injection tube, said method comprising:
   advancing the hemostatic device through the puncture until the apex is positioned to at least partially seal the puncture and the at least one guide opening is positioned outside and substantially adjacent the vessel;
   discharging a first fluid from the at least one guide opening to facilitate sealing the puncture, wherein a longitudinal axis of the at least one guide opening is angled towards a distal end of the hemostatic device such that the first fluid channeled through the injection tube is discharged towards the vessel; and
   withdrawing the hemostatic device from the puncture.

2. A method in accordance with claim 1 further comprising injecting the first fluid through a proximal tube opening of the injection tube.

3. A method in accordance with claim 2 further comprising actuating a tube valve to selectively provide access to the proximal tube opening.

4. A method in accordance with claim 1, wherein advancing the hemostatic device further comprises advancing the hemostatic device until a second fluid is channeled through a distal device opening of a locator device.

5. A method in accordance with claim 1, wherein advancing the hemostatic device further comprises advancing the hemostatic device until a second fluid is discharged from a proximal device opening of a locator device.

6. A method in accordance with claim 5 further comprising actuating a device valve to selectively restrict access to the proximal device opening.

7. A method in accordance with claim 1 further comprising:
   advancing a guidewire through the puncture; and
   advancing the hemostatic device along the guidewire.

8. A hemostatic device for sealing a puncture of a vessel, said hemostatic device comprising:
   an injection tube defining a lumen and having at least one distal tube opening, the lumen configured to channel a first fluid comprising at least one of a hemocoagulant agent, a sealant, and a flowable gelatin through the at least one distal tube opening to facilitate sealing the puncture; and
   a guide adjacent the at least one distal tube opening of the injection tube, the guide comprising a first cone-shaped portion having an apex oriented towards a distal end of the hemostatic device, the apex configured to at least partially seal the puncture, wherein at least one guide opening is defined in the first cone-shaped portion in fluid communication with the at least one distal tube opening, a longitudinal axis of the at least one guide opening is angled towards a distal end of the hemostatic device such that the first fluid is dischargeable from the at least one guide opening towards the vessel from outside the vessel when the apex is positioned to at least partially seal the puncture.

9. A hemostatic device in accordance with claim 8, wherein the injection tube has a proximal tube opening in fluid communication with the lumen and the at least one guide opening including a plurality of guide openings spaced substantially evenly about a circumference of the guide.

10. A hemostatic device in accordance with claim 9 further comprising a tube valve actuatable to selectively provide access to the proximal tube opening.

11. A hemostatic device in accordance with claim 8 further comprising a locator device having a distal device opening configured to channel a second fluid therethrough.

12. A hemostatic device in accordance with claim 11, wherein the guide comprises a second cone-shaped portion having an apex oriented towards a proximal end of the hemostatic device, the guide located between the at least one distal tube opening and the distal device opening.

13. A hemostatic device in accordance with claim 11, wherein the locator device is coupled to at least one of the injection tube and the guide such that the guide is positionable outside and substantially adjacent the vessel when the distal device opening is within the vessel, the at least one guide opening oriented such that an angle between a longitudinal axis of the at least one guide opening and a longitudinal axis of at least one of the locator device and the injection tube is approximately 45 degrees.

14. A hemostatic device in accordance with claim 8 further comprising a locator device having a proximal device opening configured to discharge a second fluid therefrom.

15. A hemostatic device in accordance with claim 14 further comprising a device valve actuatable to selectively restrict access to the proximal device opening.

16. A system for sealing a puncture of a vessel, said system comprising:
   a guidewire; and
   a hemostatic device comprising an injection tube and a guide adjacent a distal end of the injection tube, the injection tube defining a lumen and having at least one distal tube opening, the lumen configured to channel a first fluid comprising at least one of a hemocoagulant agent, a sealant, and a flowable gelatin through the at least one distal tube opening, the guide comprising a cone-shaped portion having an apex oriented towards a distal end of the hemostatic device, the apex configured to at least partially seal the puncture, wherein at least one guide opening is defined in the cone-shaped portion in fluid communication with the at least one distal tube opening, a longitudinal axis of the at least one guide opening is angled towards a distal end of the hemostatic device such that the first fluid is dischargeable from the at least one guide opening towards the vessel from outside the vessel when the apex is positioned to at least partially seal the puncture, wherein the hemostatic device is configured to be advanced along the guidewire.

17. A system in accordance with claim 16, wherein the hemostatic device further comprises a tube valve that is actuatable to selectively provide access to a proximal tube opening of the injection tube, the proximal tube opening in fluid communication with the lumen, the at least one guide opening including a plurality of guide openings spaced substantially evenly about a circumference of the guide.

18. A system in accordance with claim 16, wherein the hemostatic device further comprises a locator device having a distal device opening configured to channel a second fluid therethrough, the guide comprising a second cone-shaped portion having an apex oriented towards a proximal end of the hemostatic device, the guide located between the at least one distal tube opening and the distal device opening.

19. A system in accordance with claim 18, wherein the locator device is coupled to at least one of the injection tube and the guide such that the guide is positionable outside and substantially adjacent the vessel when the distal device opening is within the vessel, the at least one guide opening oriented such that an angle between a longitudinal axis of the at least one guide opening and a longitudinal axis of at least one of the locator device and the injection tube is approximately 45 degrees.

20. A system in accordance with claim 16, wherein the hemostatic device further comprises a locator device having a proximal device opening configured to discharge a second fluid therefrom, and a device valve that is actuatable to selectively restrict access to the proximal device opening.

* * * * *